US00PP35763P3

(12) United States Plant Patent
Perrault et al.

(10) Patent No.: US PP35,763 P3
(45) Date of Patent: Apr. 23, 2024

(54) HOP PLANT NAMED 'HBC 1134'

(50) Latin Name: *Humulus lupulus*
Varietal Denomination: HBC 1134

(71) Applicant: HOP BREEDING COMPANY, L.L.C., Yakima, WA (US)

(72) Inventors: Jason Perrault, Toppenish, WA (US); Michael D. Ferguson, Yakima, WA (US); Scott Varnum, Ellensburg, WA (US); Jaime Avalos P., Granger, WA (US); Scott Herzog, Yakima, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 17/803,908

(22) Filed: Jan. 13, 2023

(65) Prior Publication Data

US 2023/0309429 P1 Sep. 28, 2023

Related U.S. Application Data

(60) Provisional application No. 63/361,737, filed on Jan. 14, 2022.

(51) Int. Cl.
*A01H 5/02* (2018.01)
*A01H 6/28* (2018.01)

(52) U.S. Cl.
USPC ..... Plt./236
CPC ..... *A01H 6/28* (2018.05); *A01H 5/02* (2013.01)

(58) Field of Classification Search
USPC ..... Plt./236
CPC ..... A01H 5/02; A01H 5/08
See application file for complete search history.

*Primary Examiner* — Kent L Bell
(74) *Attorney, Agent, or Firm* — Svendsen Legal, LLC

(57) ABSTRACT

A new hop plant named 'HBC 1134' is disclosed. 'HBC 1134' is used for its exceptional and unique aromatic qualities, and is suitable for beer flavoring.

6 Drawing Sheets

Genus and species: *Humulus lupulus*.
Variety denomination: 'HBC 1134'.

STATEMENT REGARDING FEDERALLY SPONSORED RESEARCH OR DEVELOPMENT

None

BACKGROUND OF THE INVENTION

'HBC 1134' is a product of a controlled breeding program carried out by the inventors in the Yakima Valley of Washington State. 'HBC 1134' was one of several seedlings resulting from a controlled cross made in 2016 with female parent 'Hersbrucker Pure' (Not Patented), and male parent '15.161.49BM' (Not Patented). Seedling plants from this cross were planted in 2017 and screened for disease resistance and sex in a greenhouse and field nursery near Granger, Washington. A single plant of 'HBC 1134' was selected in 2017. In 2018 'HBC 1134' was asexually reproduced via softwood cuttings and expanded to a seven hill plot. In 2020, 'HBC 1134' was asexually reproduced via softwood cuttings, and expanded to 30 plants in an evaluation block near Toppenish, Washington. In 2021, 'HBC 1134' was further expanded to a one acre test block near Toppenish, Washington with plants also asexually reproduced via softwood cuttings. The 'HBC 1134' plants have now been observed and evaluated for several years. Throughout several generations of asexual propagation, 'HBC 1134' has been observed to retain its distinctive characteristics and remain true to type.

SUMMARY OF THE INVENTION

A new and distinct hop plant is described herein, with the 'HBC 1134' cultivar characterized by having cones with a high alpha acid content. The new cultivar exhibits spicy, citrus, floral, woody, and herbal aromas. The new cultivar is suitable for beer flavoring.

BRIEF DESCRIPTION OF THE PHOTOGRAPHS

Figure 1:
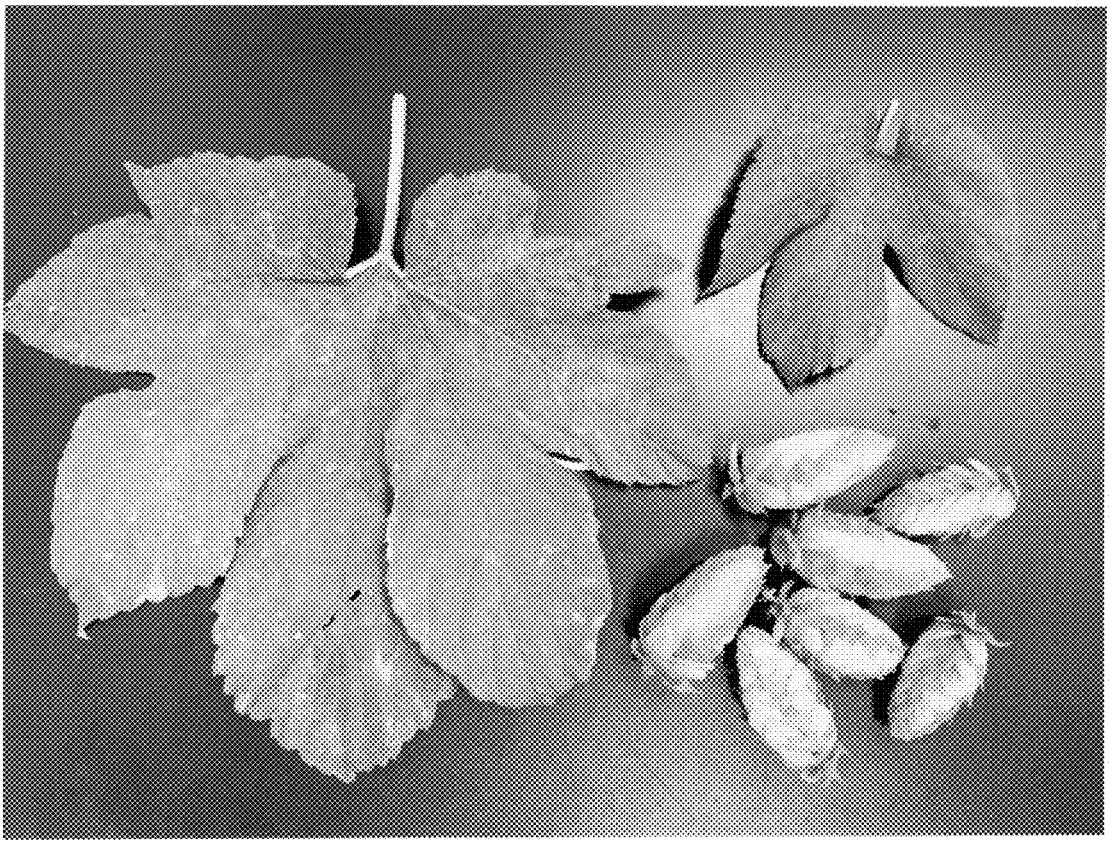
FIG. 1 illustrates a close up of mature leaves and cones of a 'HBC 1134' hop plant at approximately four months of vegetative growth.
Figure 2:
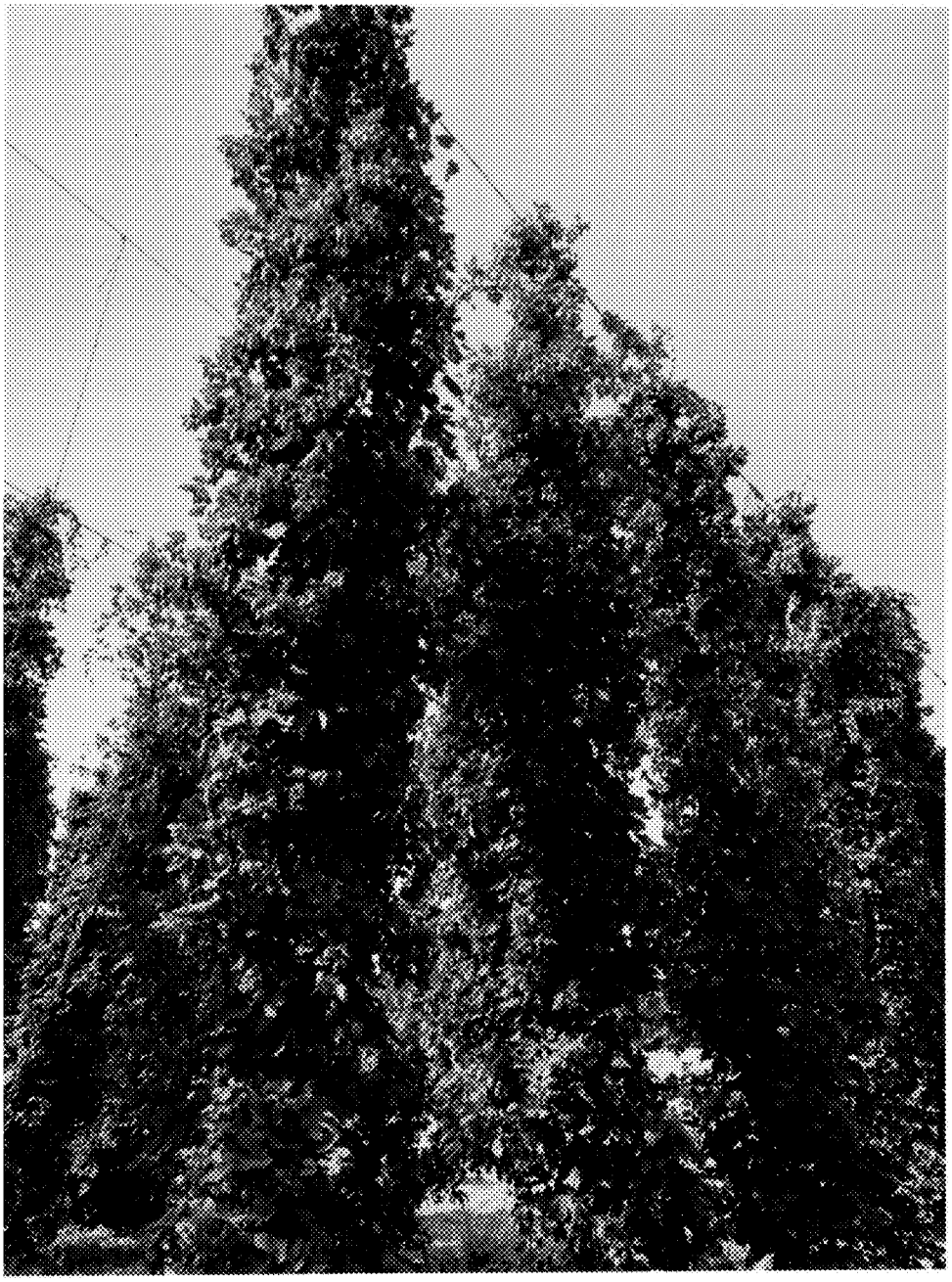
FIG. 2 illustrates a multiple of trellis with maturing 'HBC 1134' hop plant bines at approximately three months of vegetative growth.
Figure 3:
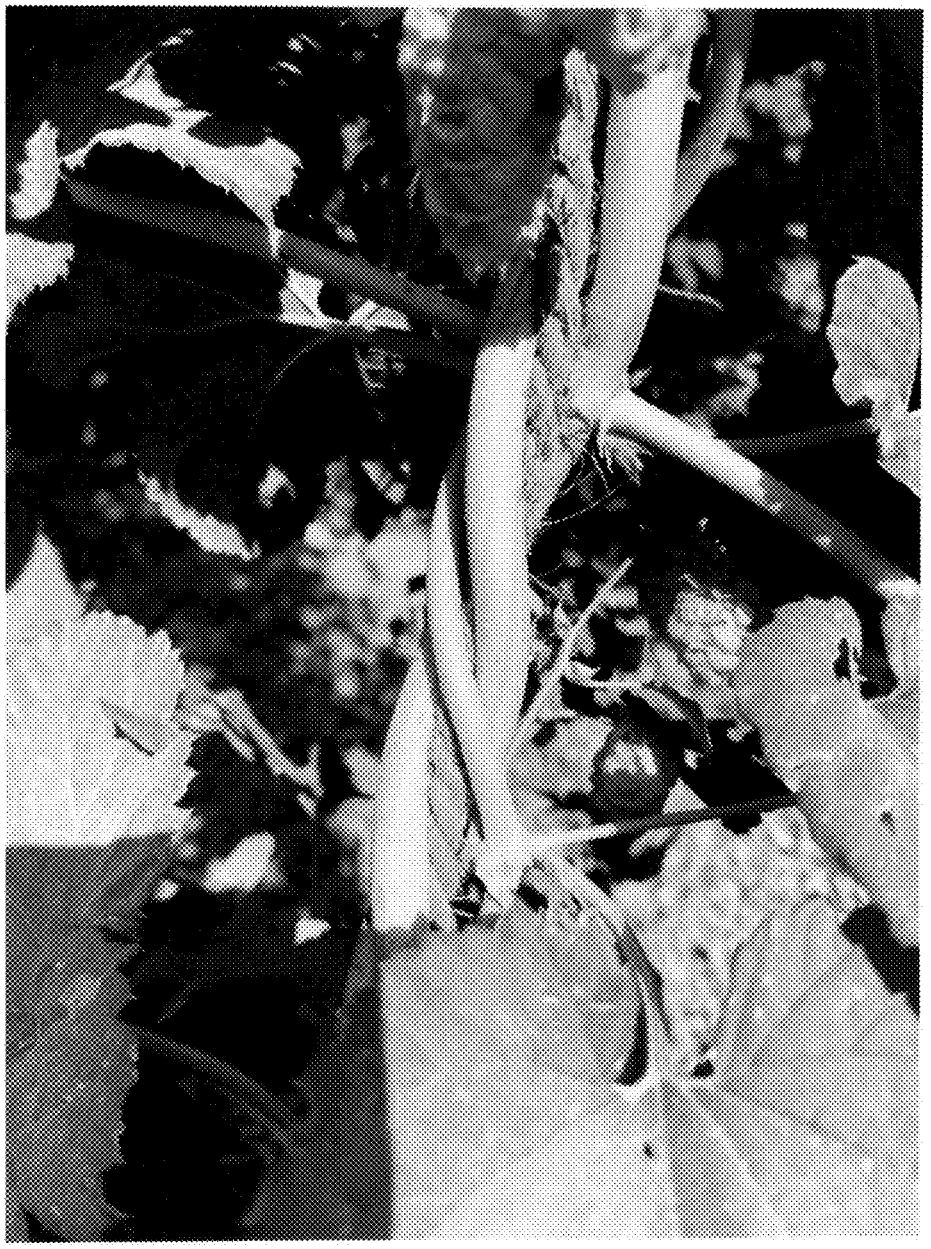
FIG. 3 illustrates a close up of a bine of a maturing 'HBC 1134' hop plant at approximately three months of vegetative growth on a trellis.
Figure 4:
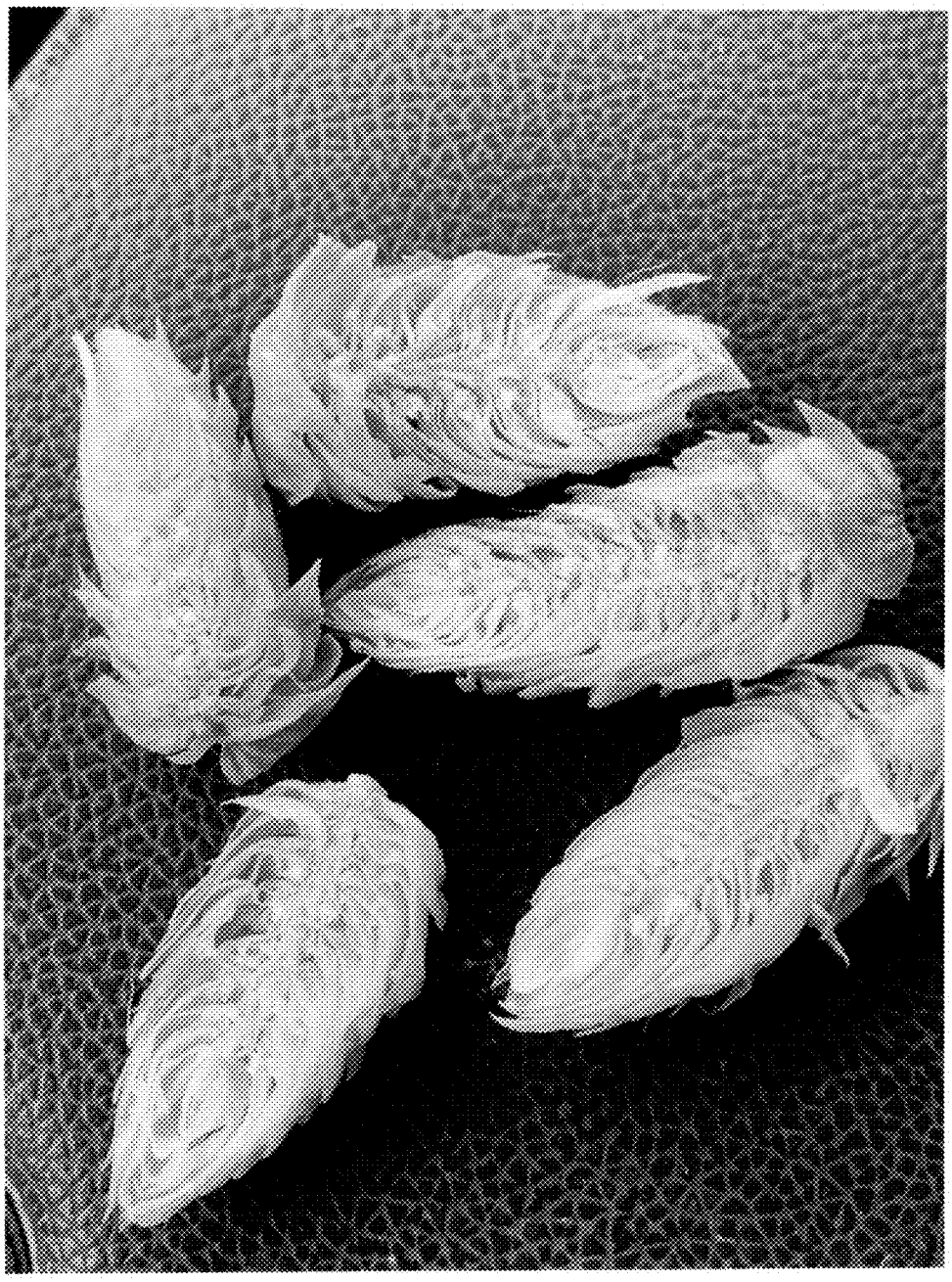
FIG. 4 illustrates cross-sectioned mature cones of a 'HBC 1134' hop plant at approximately four months of vegetative growth.
Figure 5:
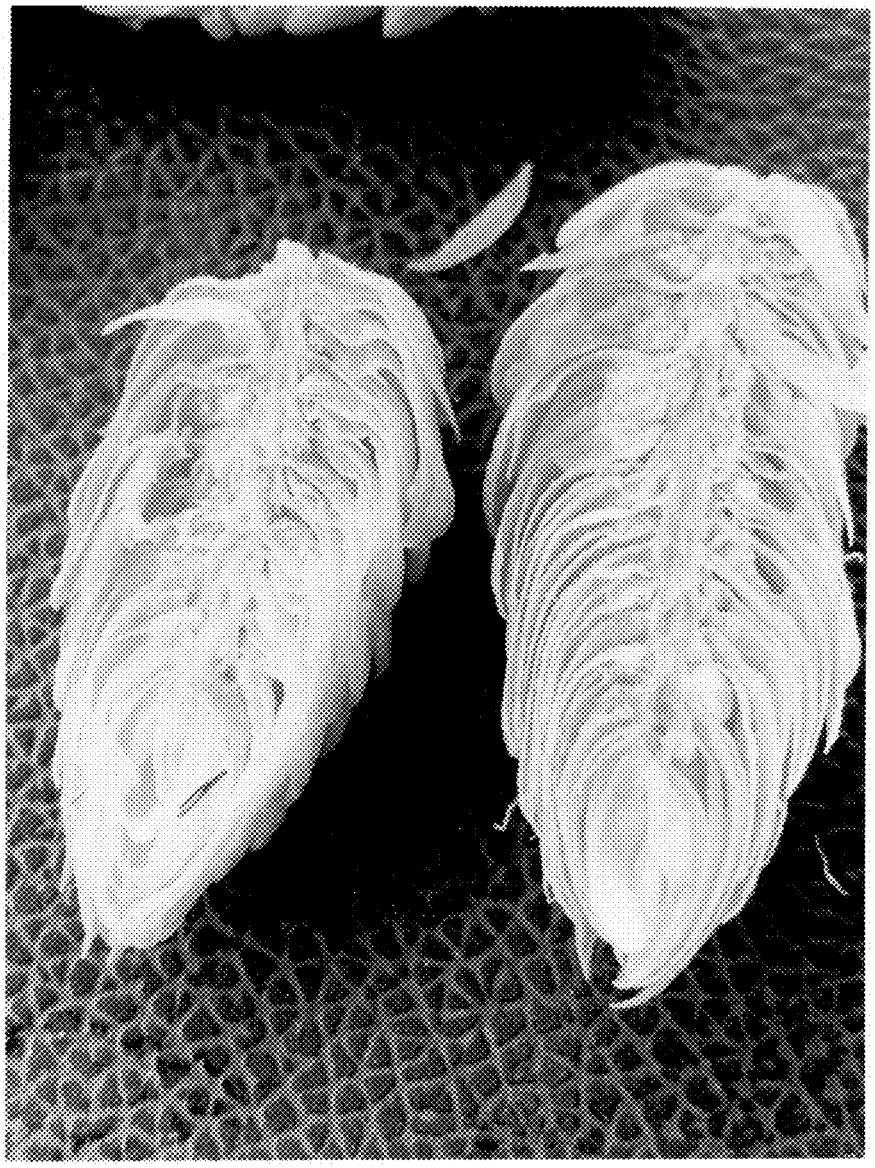
FIG. 5 illustrates a close up of cross-sectioned mature cones of a 'HBC 1134' hop plant at approximately four months of vegetative growth.
Figure 6:
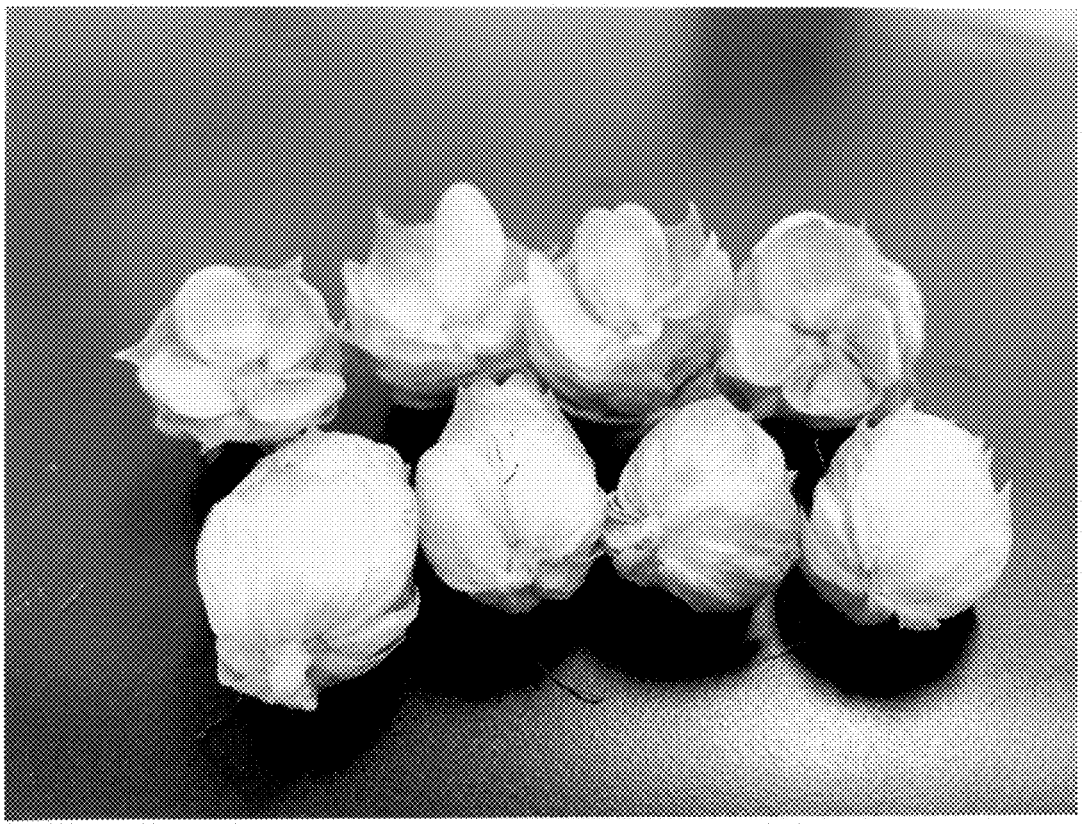
FIG. 6 illustrates a close up of cross-sectioned mature cones of a 'HBC 1134' hop plant at approximately four months of vegetative growth.

The colors of these illustrations may vary produce lighting conditions and, therefore, color characteristics of this new variety should be determined with reference to the observations described herein, rather than from these illustrations alone.

COMPARISON OF 'HBC 1134' TO PARENT PLANT AND COMPARISON CULTIVAR

'HBC 1134' has many aroma and flavor characteristics that are similar to its female parent, the cultivar 'Hersbrucker Pure'. It is distinguished from 'Hersbrucker Pure' by having much higher alpha acids (with alpha acids of approximately 11% percent of cone weight typical for 'HBC 1134', versus alpha acids of approximately 5% percent of cone weight typical for 'Hersbrucker Pure'). Also, 'HBC 1134' is much more vigorous, higher yielding, and with a heavier and larger cone size, as compared to 'Hersbrucker Pure'.

'HBC 1134' is distinguishable from its male parent '15.161.49BM' with flowers that develop into mature hop cones without producing pollen, while flowers of '15.161.49BM' produce pollen without developing into mature hop cones.

Table 1. below, sets forth some of the distinguishing characteristics of 'HBC 1134' as observed, as compared to its female parent 'Hersbrucker Pure', and to the 'COLUMBUS' (U.S. Plant Pat. No. 10,956) cultivar as a closely comparable cultivar.

TABLE 1

| | INSTANT CV. 'HBC 1134' | FEMALE PARENT 'Hersbrucker Pure' | COMPARISON CV. 'COLUMBUS' |
|---|---|---|---|
| Alpha (% of cone weight) | 10.9 | 4.7-6.0 | 14.5-17.5 |
| Beta (% of cone weight) | 4.0 | 2.0-3.0 | 4.5-6.0 |
| Co-humulone (% of alpha acids) | 29.1 | 20-28 | 28-30 |
| Total Oil (mL/100 g) | 2.1 | 0.6-1.2 | 2.5-4.5 |
| Aroma Profile | spicy, citrus, floral, woody, herbal | floral, herbal, spice | earthy, citrus, spicy |

DETAILED BOTANICAL DESCRIPTION

The following description is based on observations made in August of 2021 near Granger, Washington, on mature plants at approximately four months of vegetative growth. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, published by The Royal Horticultural Society of Great Britain.

Ploidy: Diploid.

Sex: Female.

Use: Brewing beer and ale.

Observed yield: 2,200 to 3,200 pounds per acre.

Plant shape: Cylindrical.

Growth type: Normal.

Disease and pest resistance or susceptibility:

*Powdery mildew* (*Podosphaera macularis*).—Tolerant.

Hardiness: Observed Plant Hardiness Zone 7a to 6b.

Freeze tolerance: Typically intolerant of freezing temperatures during the growing season.

Table of oil analytical characteristics (averages or ranges):

TABLE 2

| | |
|---|---|
| % Alpha Acid (% cone weight) | 10.9 |
| % Beta Acid (% cone weight) | 4.0 |
| % Cohumulone (% alpha acids) | 29.1 |
| A-Pinene (% of total oils) | 0.09 to 0.15 |
| B-Pinene(% of total oils) | 0.72 to 1.03 |
| Myrcene (% of total oils) | 47.04 to 71.89 |
| Humulene (% of total oils) | 9.09 to 12.87 |
| Caryophyllene Oxide (% of total oils) | 0.03 to 0.22 |
| Farnesene (% of total oils) | 0.8 to 0.14 |
| Linalool (% of total oils) | 0.36 to 0.49 |
| Total Oil (ml/100 g of cones): | 2.1 |
| Hop Storage Index (% loss) | 27.1 |
| Aroma Profile | Noble (Spicy, Citrus, Floral, Woody, and Herbal.) |

Bine:

*Bine color*.—Yellow-Green 145C.

*Stripe present*.—Yes.

*Stripe color*.—Dark Green-Brown 152D.

*Stipule direction*.—Interpetiolar.

*Stipule color*.—Yellow-Green 145B.

*Stipules per bine*.—54.

*Typical bine length*.—5.5 m.

*Typical internode length on bine*.—12 cm to 15 cm.

*Typical internode length on lateral*.—7 cm.

*Bine diameter*.—7 mm at base; 7 mm at nine feet; and 7 mm at terminal end of eighteen feet.

*Average lateral length* (*on bottom third of plant*).—65 cm.

*Average lateral length* (*on middle third of plant*).—75 cm.

*Average laterals length* (*on upper third of plant*).—65 cm.

*Lateral density* (*on middle third of plant*).—Medium (two laterals per node)].

*Average lateral length*.—65 cm to 75 cm.

*Lateral density at middle third of plant*.—Two Laterals per Node.

*Anthocyanin coloration on main bine*.—Absent.

Leaf:

*Arrangement*.—Opposite.

*Shape*.—Palmately Lobed.

*Apex*.—Cuspidate.

*Base*.—Sagitate.

*Margin*.—Serrated.

*Serrations per inch* (*typically*).—5.

*Pose*.—Horizontal.

*Average length of mature leaf*.—17.5 cm.

*Average width of mature leaf*.—15 cm.

*Leaf blistering on the upper side of leaf blade*.—Absent.

*Color of mature leaf upper surface*.—Green 139A.

*Color of mature leaf lower surface*.—Green 139A.

*Color of immature leaf upper surface*.—Green 139A.

*Color of immature leaf lower surface*.—Green 139A.

*Number of lobes*.—7.

*Petiole color at base*.—Yellow-Green 139C.

*Average petiole diameter* (*mature*).—3 mm.

*Average petiole length* (*mature, typical*).—4.5 cm.

*Venation*.—Palmate.

*Vein color*.—Yellow-Green 146C.

Cone:

*Cone shape*.—Ovate.

*Average cone length*.—3.5 cm.

*Average cone diameter.*—1.7 cm.
*Typical cone weight.*—0.85 g.
*Bract shape*.—Aristate.
*Bract base shape*.—Rounded.
*Bract margin*.—Entire.
*Bract tip shape*.—Cuspidate.
*Bract tip position*.—Alternating.
*Degree of bract opening*.—Slightly Open.
*Bract tip color*.—Green N143C.
*Bract base color*.—Green N145C.
*Bract length.*—14 mm.
*Bract width.*—12 mm.
*Bracteole shape*.—Ovate.
*Bracteole length.*—9 mm.
*Bracteole width.*—14 mm.
*Bracteole color* (*upper surface*).—Green N145B.
*Bracteole color* (*lower surface*).—Green N144C.
*Lupulin glands shape*.—Pedunculated Oblong Polyps.
*Lupulin glands color*.—Yellow-Orange 21C.
*Number of lupulin glands per cone*.—Varies Greatly (Moderate to Many) with approximately 50,000 lupulin glands per Cone.
*Pickability*.—Good.
*Time of flowering*.—Late July.
*Maturity date range* (*early, medium, late*).—Early.
*Harvest dates*.—Typically harvested September 8 to September 15, but can deviate from this time period, depending on growing practices and location.

What is claimed:

1. A new and distinct variety of Hop plant named 'HBC 1134', substantially as illustrated and described herein.

* * * * *